United States Patent
Yang et al.

(10) Patent No.: US 10,668,069 B2
(45) Date of Patent: Jun. 2, 2020

(54) PHARMACEUTICAL COMPOSITION COMPRISING NEPTINIB OR SALT THEREOF AND METHOD FOR CONTROLLING IMPURITY THEREOF

(71) Applicant: SHENZHEN NEPTUNUS PHARMACEUTICAL RESEARCH INSTITUTE CO., LTD., Shenzhen, Guangdong (CN)

(72) Inventors: Jingan Yang, Guangdong (CN); Zhiguo Wang, Guangdong (CN); Jing Cui, Guangdong (CN); Xiaorou Liu, Guangdong (CN)

(73) Assignee: SHENZHEN NEPTUNUS PHARMACEUTICAL RESEARCH INSITUTE CO., LTD, Shenzhen, Guangdong (CN)

( * ) Notice: Subject to any disclaimer, the term of this patent is extended or adjusted under 35 U.S.C. 154(b) by 0 days.

(21) Appl. No.: 16/330,337

(22) PCT Filed: Sep. 1, 2017

(86) PCT No.: PCT/CN2017/100189
§ 371 (c)(1),
(2) Date: Mar. 4, 2019

(87) PCT Pub. No.: WO2018/041246
PCT Pub. Date: Mar. 8, 2018

(65) Prior Publication Data
US 2019/0224201 A1 Jul. 25, 2019

(30) Foreign Application Priority Data
Sep. 5, 2016 (CN) .......................... 2016 1 0801047

(51) Int. Cl.
| | | |
|---|---|---|
| A61K 31/517 | (2006.01) |
| A61K 9/00 | (2006.01) |
| A61K 47/36 | (2006.01) |
| A61K 47/38 | (2006.01) |
| A61K 47/12 | (2006.01) |
| A61K 47/14 | (2017.01) |
| A61P 35/00 | (2006.01) |
| A61K 47/26 | (2006.01) |
| A61K 9/20 | (2006.01) |
| A61K 9/28 | (2006.01) |

(52) U.S. Cl.
CPC .............. *A61K 31/517* (2013.01); *A61K 9/00* (2013.01); *A61K 9/2009* (2013.01); *A61K 9/2018* (2013.01); *A61K 9/2027* (2013.01); *A61K 9/2054* (2013.01); *A61K 9/2866* (2013.01); *A61K 47/12* (2013.01); *A61K 47/14* (2013.01); *A61K 47/26* (2013.01); *A61K 47/36* (2013.01); *A61K 47/38* (2013.01); *A61P 35/00* (2018.01)

(58) Field of Classification Search
CPC ...... A61K 9/00; A61K 9/2009; A61K 9/2018; A61K 9/2027; A61K 9/2054; A61K 9/2866; A61K 47/12; A61K 47/14; A61K 47/26; A61K 47/36; A61K 47/38; A61K 31/517; A61P 35/00
See application file for complete search history.

(56) References Cited

U.S. PATENT DOCUMENTS 8,883,800 B2 * 11/2014 Pfrengle .............. A61K 31/522
514/258.1

FOREIGN PATENT DOCUMENTS

WO WO-2016101867 A1 * 6/2016 ........... C07D 239/94

\* cited by examiner

*Primary Examiner* — Ali Soroush
(74) *Attorney, Agent, or Firm* — Greer, Burns & Crain, Ltd.

(57) ABSTRACT

A pharmaceutical composition including neptinib is provided. The composition includes neptinib or a pharmaceutically acceptable salt thereof, and an excipient at a low risk of compatibleness. Furthermore, the pharmaceutical composition of the present invention may also include pharmaceutically acceptable organic acid or inorganic acid as a stabilizer. The content of impurity A maintains a non-significant increase in the long-term and accelerated stability investigation for the pharmaceutical composition.

7 Claims, No Drawings

PHARMACEUTICAL COMPOSITION COMPRISING NEPTINIB OR SALT THEREOF AND METHOD FOR CONTROLLING IMPURITY THEREOF

FIELD OF THE INVENTION

The present invention relates to a kind of pharmaceutical composition.

BACKGROUND (E)-N-(4-((3-chloro-4-fluorophenyl)amino)-7-ethoxyquinazolin-6-yl)-4-(di methylamino)but-2-enamide having the structure as shown in the formula (II), is a newly developed "tinib" drug for EGFR-mutated non-small cell lung cancer as well as EGFR-mutated and Her2-overexpressed non-small cell lung cancer, and it is named neptinib. The remarkable feature of neptinib and its acceptable salts such as dimaleate, xylenesulfonate and hydrochloride is that it is highly prone to produce a specific impurity A, whose possible structure has been identified as shown in the formula (I):

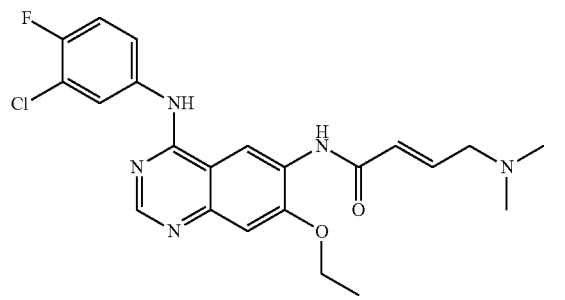

(II)

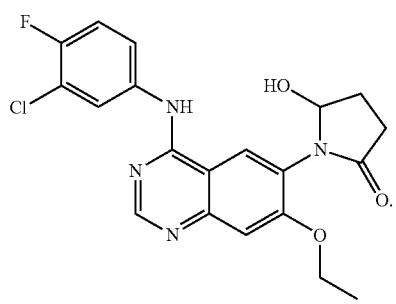

(I)

Taking the main ingredient itself as a control, the relative retention time of impurity A is about 0.50-0.52. More particular, through the study of neptinib and its salt forms and crystal forms, a salt-type active ingredient with a stable crystal form has been identified. When only the active ingredient is present, its properties are relatively stable, and under the influence of various factors or after an accelerated stability test at 40° C. for 6 months, there is no significant change in the content of impurities in the active ingredient. However, when the active ingredient is combined with excipients, its stability tend to lowered, and impurity A emerges very easily which accounts for the largest amount of impurity in the active ingredient.

In order to prevent significant increase in the content of impurity A, through extensively compatibility studies of the active ingredient neptinib or its salt with excipients, the present inventors finally has found a group of compositions with low compatibility risks. Under the condition of strictly controlled storage temperature, the content of impurity A produced in the composition can be controlled within the acceptable limits specified by the relevant technical guidelines. Since the lower storage temperature adds additional cost and requires special management measures for practical use, transportation and storage, in order to achieve convenient storage and transportation of neptinib preparations under relatively less strict conditions, the inventors of the present application further studied the production mechanisms of impurity A and found that based on the above compositions with a low compatibility risk, the addition of acids can inhibit the production of impurity A, thereby better controlling the content of impurity A in the composition.

SUMMARY

The object of the present invention is to provide a pharmaceutical composition comprising neptinib. The pharmaceutical composition comprises neptinib or a pharmaceutically acceptable salt thereof, and one or more excipients selected from the group consisting of lactose, mannitol, starch-lactose compound, microcrystalline cellulose-lactose compound, crospovidone, colloidal silica and glyceryl behenate.

In the pharmaceutical composition of the present invention, neptinib is an active free base, and its acceptable salt refers to various salts formed by the free base and acid radicals. Such acid radicals include, but are not limited to, hydrochloric acid, toluenesulfonic acid, dimaleic acid, acetic acid, succinic acid, sulfonic acid, methanesulfonic acid and trifluoromethanesulfonic acid. In the present invention, preferred salt is xylenesulfonate, especially a hydrate of xylenesulfonate, and the most preferred is a xylenesulfonate containing 1.0-1.5 crystal water in its molecule.

In the pharmaceutical composition of the present invention, the amount of neptinib or a pharmaceutically acceptable salt thereof is preferably 0.05%-12% (by weight), and more preferably 0.1%-7% (by weight).

In a preferred embodiment, the pharmaceutical composition comprising neptinib of the present invention comprises the following components by weight:

Neptinib or a pharmaceutically acceptable salt thereof 0.1%-7%

Lactose and mannitol combination 70-96%

Crospovidone 1-10%

Colloidal silica 0.5-3%

Glyceryl behenate 0.5-3%.

Further, the composition may also comprise a pharmaceutically acceptable organic or inorganic acid as a stabilizer. The content of impurity A maintains at low level and does not increase significantly in the long-term and accelerated stability tests for the pharmaceutical composition, and the impurity A has the structure as shown in the formula (I):

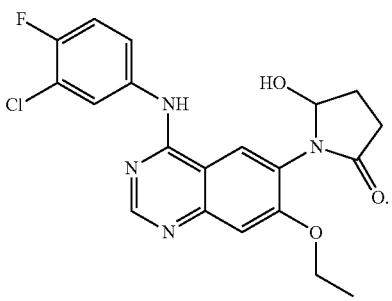

(I)

In a preferred embodiment, the pharmaceutical composition comprising neptinib of the present invention comprises the following components by weight:

Neptinib or a pharmaceutically acceptable salt thereof 0.1%-7%

Filler 55%-90%

Disintegrant 1%-10%

Glidant 0.5%-3%

Lubricant 0.5%-3%

Stabilizer 0.1%-15%;

wherein the filler is one or more selected from the group consisting of lactose, mannitol, starch-lactose compound, and microcrystalline cellulose-lactose compound; the disintegrant is crospovidone XL or XL-10; the lubricant is glyceryl behenate; the glidant is colloidal silica; and the stabilizer is selected from the group consisting of benzoic acid, citric acid, tartaric acid, malic acid, edetic acid, and lactic acid.

The stabilizing agent in the pharmaceutical composition of the present invention is preferably selected from the group consisting of citric acid, tartaric acid and malic acid.

In order to obtain a pharmaceutical composition of neptinib with stable properties and limited degradation, the inventors of the present application conducted extensive compatibility studies of the active ingredient of the pharmaceutical composition with various excipients. The inventors of the present application found that impurity A is generated significantly which has to be slickly controlled. According to the compatibility studies, the inventors identified a group of excipients which can be used for formulation development with low degradation risks, including lactose, mannitol, starch-lactose compound, microcrystalline cellulose-lactose compound, crospovidone, colloidal silica, and glyceryl behenate.

It is satisfactory that the content of impurity A and other impurities in the obtained composition is identical to that in the active ingredient at day 0. The obtained composition and its dosage forms according to the present invention can still meet the limit requirement after an accelerated stability test at a lower temperature (30±12° C., RH 65±15%) for 6 months, indicating that the dosage forms can be stored for a long period of time at a temperature below 25° C.

Since the lower storage temperature adds additional costs and requires special management measures for practical use, transportation and storage, the inventors have conducted further studies on the degradation mechanism of impurity A, which is shown in the following reaction scheme (1):

Reaction scheme (1).

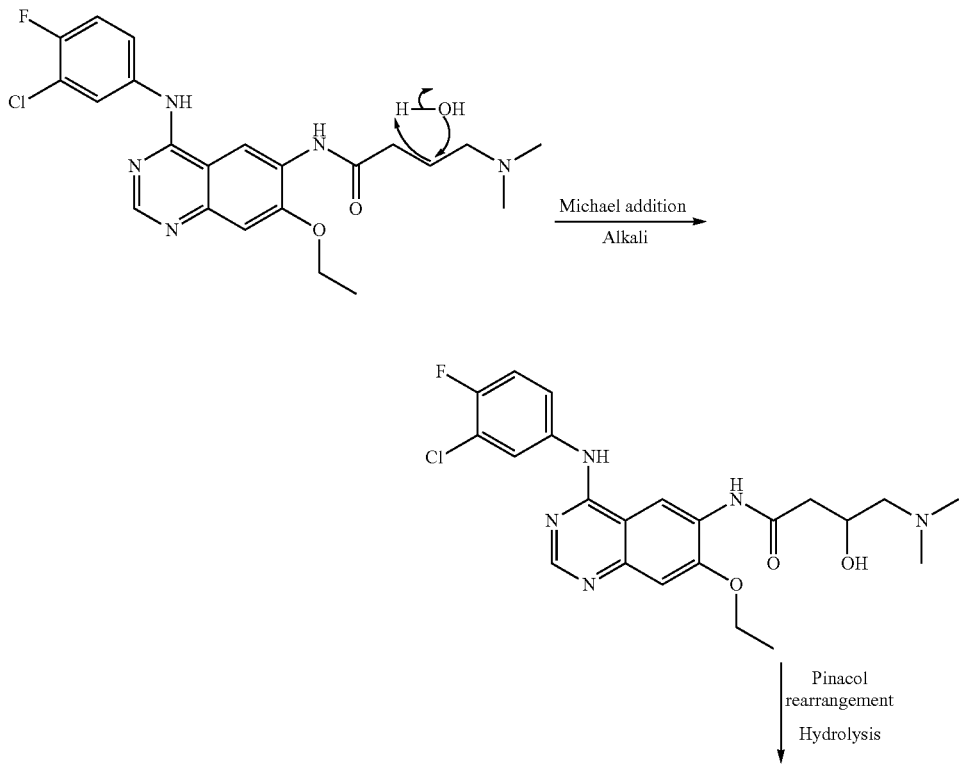

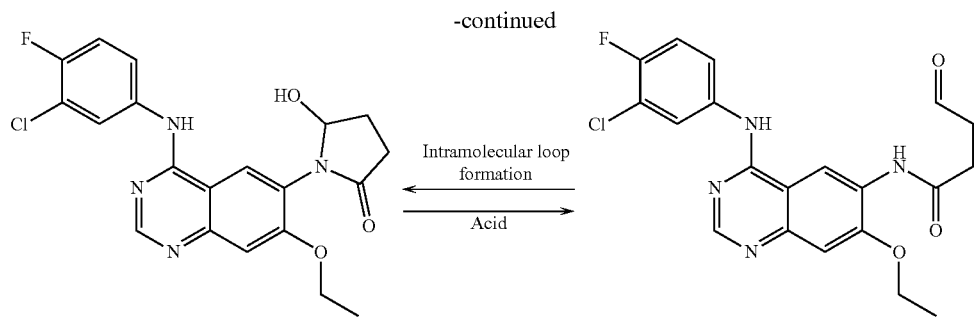

If the microenvironment of the active ingredient neptinib or its salts is alkaline, the impurity A is easily generated, and the reaction is continuous and will not be suppressed by the accumulation of the degradation product. Further, the inventors have found that the addition of certain inorganic or organic acids to the above-mentioned composition comprising the active ingredient neptinib or its salts and the excipients selected in the present invention can suppress the generation of impurity A, and thus the acid can be used as a stabilizer. Therefore, a pharmaceutically acceptable organic or inorganic acid as a stabilizer is added to the composition, wherein the organic or inorganic acid is selected from the group consisting of benzoic acid, citric acid, tartaric acid, malic acid, edetic acid and lactic acid. Such pharmaceutical composition can control the generation of impurities and the long-term stability of the pharmaceutical composition is improved.

The compositions provided by the present invention are suitably formulated into solid preparations including tablet, capsule, granule and powder, wherein the tablet, in particular, contain a HPMC film coating.

The stability of the active ingredient limits the preparation process. For example, the active ingredient neptinib or its salts are sensitive to moisture and heat, so processes such as wet granulation and drying should be avoided in the preparation process. In the embodiments of the present invention, preparation methods such as direct compressing or direct filling are preferred. In addition, the possible changes in the crystal form of the active ingredient should also be considered. The preparation method of the tablet is determined by the properties of the active ingredient, and a preparation process that can maintain the stability of the active ingredient is preferred. In the practice of the present invention, dry granulation and then compression process or direct powder compression process is preferred, and direct powder compression is the most preferred. The preparation process includes sieving, mixing, and compressing process, and does not involve heat and moisture treatments, ensuring the maximum stability of the active ingredient. The tablet may be film-coated if needed, and the formulation of the film coating is preferably as simple as possible, wherein the film material in the coating formulation is preferably HPMC. The plasticizer in the coating formulation is preferably an ester, such as triacetin, triethyl citrate. The color ingot in the coating formulation is preferably titanium dioxide. The ideas of the preparation method of the capsules are also consistent with that of the tablets, that is the moisture and heat is avoided, direct powder filling is preferred and suitable excipients having good fluidity should be selected. Depending on the weight of the contents to be filled, gelatin capsules sizes 1# to 4# or HPMC capsules may be chosen. The granules can be obtained by conventional granulation techniques, such as wet granulation, dry granulation or fluid bed granulation followed by packing into suitable package bags. The powder is obtained by mixing the active ingredient and the excipients and then directly packing it into suitable package bags under the premise of uniform mixing.

DETAILED DESCRIPTION

Examples

The following examples are intended to facilitate the person skilled in the art to fully understand the technical solution and the intent of the invention, in stead of limiting the scope of the invention. The active ingredient (API, neptinib xylenesulfonate) used in Examples 1-3 was synthesized in pilot-scale by the inventors according to the methods described in Chinese Patent No. ZL201410822395.3 and ZL 201410826075.5, with the content of 99.8%-100.3% and moisture of 3.0-3.1% (determined by Karl Fischer method). Other related excipients are commercially available products.

Example 1: Selection of Excipients

TABLE 1

Results of API and excipients compatibility study

| | | Day 0 | | Day 10 | | | | | | | |
| | | | | RH75% ± 5% | | RH92.5% ± 5% | | 60° C. ± 2° C. | | Illumination (4500 ± 500 lx) | |
| Name | API/ excipient ratio | Maximum single impurity (%) | Total impurity (%) | Maximum single impurity (%) | Total impurity (%) | Maximum single impurity (%) | Total impurity (%) | Maximum single impurity (%) | Total impurity (%) | Maximum single impurity (%) | Total impurity (%) |
| --- | --- | --- | --- | --- | --- | --- | --- | --- | --- | --- | --- |
| API | / | 0.02 RRT1.21 | 0.02 | 0.02 RRT1.21 | 0.02 | 0.02 RRT1.22 | 0.02 | 0.02 RRT1.21 | 0.04 | 0.12 RRT0.93 | 0.14 |

TABLE 1-continued

Results of API and excipients compatibility study

| Name | API/ excipient ratio | Day 0 Maximum single impurity (%) | Day 0 Total impurity (%) | Day 10 RH75% ± 5% Maximum single impurity (%) | Day 10 RH75% ± 5% Total impurity (%) | Day 10 RH92.5% ± 5% Maximum single impurity (%) | Day 10 RH92.5% ± 5% Total impurity (%) | Day 10 60° C. ± 2° C. Maximum single impurity (%) | Day 10 60° C. ± 2° C. Total impurity (%) | Day 10 Illumination (4500 ± 500 1x) Maximum single impurity (%) | Day 10 Illumination (4500 ± 500 1x) Total impurity (%) |
|---|---|---|---|---|---|---|---|---|---|---|---|
| Lactose | 1:10 | 0.02 RRT1.22 | 0.02 | 0.02 RRT1.21 | 0.02 | 0.02 RRT1.21 | 0.06 | 0.04 RRT0.51 | 0.06 | 0.16 RRT0.93 | 0.26 |
| Microcrystalline cellulose | 1:10 | 0.02 RRT1.22 | 0.02 | 0.05 RRT0.93 | 0.08 | 0.04 RRT0.51 | 0.08 | 1.19 RRT0.51 | 1.21 | 0.13 RRT0.93 | 0.20 |
| Microcrystalline cellulose-lactose compound | 1:10 | 0.02 RRT1.22 | 0.02 | 0.05 RRT0.93 | 0.07 | 0.04 RRT0.93 | 0.07 | 0.20 RRT0.51 | 0.22 | 0.14 RRT0.93 | 0.17 |
| Mannitol | 1:10 | 0.02 RRT1.22 | 0.02 | 0.02 RRT0.93 | 0.02 | 0.01 RRT0.52 | 0.04 | 0.04 RRT0.51 | 0.04 | 0.14 RRT0.93 | 0.23 |
| Pregelatinized starch | 1:10 | 0.02 RRT1.22 | 0.02 | 0.10 RRT0.51 | 0.14 | 0.14 RRT0.51 | 0.19 | 0.86 RRT0.51 | 0.88 | 0.11 RRT0.93 | 0.14 |
| Starch | 1:10 | 0.02 RRT1.22 | 0.02 | 0.18 RRT0.51 | 0.22 | 0.14 RRT0.51 | 0.16 | 2.53 RRT0.51 | 2.55 | 0.12 RRT0.93 | 0.22 |
| Starch-lactose compound | 1:10 | 0.02 RRT1.21 | 0.02 | 0.02 RRT1.21 | 0.03 | 0.03 RRT0.52 | 0.05 | 0.02 RRT0.52 | 0.05 | 0.14 RRT0.94 | 0.19 |
| Crospovidone | 1:10 | 0.02 RRT1.22 | 0.03 | 0.08 RRT0.33 | 0.14 | 0.06 RRT0.32 | 0.12 | 0.11 RRT0.51 | 0.15 | 0.15 RRT0.93 | 0.26 |
| Sodium carboxymethyl starch | 1:10 | 0.02 RRT1.22 | 0.02 | 0.48 RRT0.51 | 0.59 | 0.67 RRT0.51 | 0.74 | 0.35 RRT0.51 | 0.37 | 0.15 RRT0.93 | 0.33 |
| Cross-linked CMCNa | 1:10 | 0.02 RRT1.22 | 0.02 | 0.10 RRT0.51 | 0.19 | 0.05 RRT 0.81 | 0.14 | 0.12 RRT0.51 | 0.14 | 0.16 RRT0.93 | 0.32 |
| L-HPC | 1:10 | 0.02 RRT1.22 | 0.02 | 0.13 RRT0.51 | 0.20 | 0.11 RRT0.51 | 0.14 | 2.45 RRT0.52 | 2.76 | 0.14 RRT0.93 | 0.29 |
| Tartaric acid | 1:10 | 0.02 RRT1.22 | 0.02 | 0.02 RRT0.93 | 0.02 | 0.02 RRT1.21 | 0.05 | 0.04 RRT0.51 | 0.06 | 0.12 RRT0.93 | 0.21 |
| Citric acid | 1:10 | 0.02 RRT1.22 | 0.02 | 0.02 RRT1.21 | 0.02 | 0.02 RRT1.21 | 0.04 | 0.08 RRT0.51 | 0.10 | 0.14 RRT0.93 | 0.24 |
| Malic acid | 1:10 | 0.02 RRT1.22 | 0.02 | 0.04 RRT1.21 | 0.04 | 0.05 RRT1.21 | 0.06 | 0.12 RRT0.51 | 0.14 | 0.11 RRT0.93 | 0.20 |
| Magnesium stearate | 1:10 | 0.07 RRT0.66 | 0.22 | 0.04 RRT0.81 | 0.08 | 0.14 RRT0.51 | 0.23 | 0.48 RRT0.51 | 0.53 | 0.11 RRT0.93 | 0.32 |
| Sodium stearyl fumarate | 1:10 | 0.06 RRT0.51 | 0.13 | 0.08 RRT0.51 | 0.14 | 0.55 RRT0.51 | 0.65 | 18.35 RRT0.52 | 18.69 | 0.10 RRT0.93 | 0.34 |
| Glyceryl behenate | 1:10 | 0.02 RRT1.22 | 0.02 | 0.02 RRT0.93 | 0.02 | 0.02 RRT0.51 | 0.04 | 0.02 RRT0.51 | 0.02 | 0.34 RRT1.39 | 0.45 |
| Povidone | 1:10 | 0.04 RRT0.51 | 0.07 | 0.05 RRT2.53 | 0.15 | 0.08 RRT0.32 | 0.35 | 0.78 RRT0.51 | 0.99 | 0.13 RRT0.93 | 0.40 |
| Colloidal silica | 1:5 | 0.01 RRT0.93 | 0.01 | 0.04 RRT0.29 | 0.06 | 0.02 RRT0.93 | 0.03 | 0.10 RRT0.51 | 0.10 | 0.17 RRT0.93 | 0.22 |
| Empty gelatin capsule | 1:10 | 0.02 RRT1.21 | 0.02 | 0.02 RRT1.21 | 0.03 | 0.02 RRT1.21 | 0.03 | 0.38 RRT0.52 | 0.40 | 0.04 RRT0.94 | 0.06 |
| HPMC capsule | 1:10 | 0.02 RBT1.21 | 0.02 | 0.02 RRT1.21 | 0.02 | 0.02 RRT1.21 | 0.04 | 0.03 RRT0.20 | 0.07 | 0.07 RRT0.94 | 0.09 |
| API-PVA | 1:10 | 0.03 | 0.08 | 0.50 RRT0.51 | 0.61 | 0.63 RRT0.51 | 0.74 | 6.04 RRT0.51 | 6.21 | 0.12 RRT0.93 | 0.30 |
| API-HPMC | 1:10 | 0.03 | 0.07 | 0.06 RRT0.51 | 0.12 | 0.08 RRT0.51 | 0.13 | 0.91 RRT0.51 | 0.96 | 0.10 RRT0.94 | 0.14 |
| API-Triacetin | 1:10 | 0.12 | 0.19 | 0.10 RRT0.22 | 0.18 | 0.12 RRT0.22 | 0.20 | 0.10 RRT0.22 | 0.18 | 0.11 RRT0.22 | 0.23 |
| Drug-TiO₂ | 1:10 | 0.03 | 0.09 | 0.04 RRT0.51 | 0.09 | 0.06 RRT0.51 | 0.12 | 0.96 RRT0.51 | 1.80 | 0.47 RRT0.32 | 1.25 |
| Core tablet - PVA | 24.4 g:15 g | 0.03 | 0.09 | 0.19 RRT0.51 | 0.29 | 0.32 RRT0.51 | 0.48 | 1.39 RRT0.51 | 1.45 | 0.20 RRT0.94 | 0.36 |
| Core tablet - HPMC | 24.4 g:15 g | 0.03 | 0.07 | 0.07 RRT0.51 | 0.13 | 0.12 RRT0.51 | 0.31 | 0.82 RRT0.51 | 0.87 | 0.15 RRT0.94 | 0.15 |
| Core tablet - Triacetin | 24.4 g:15 g | 0.13 | 0.20 | 0.13 RRT0.22 | 0.18 | 0.13 RRT0.22 | 0.18 | 0.13 RRT0.22 | 0.22 | 0.30 RRT1.46 | 0.63 |
| Core tablet - TiO₂ | 24.4 g:15 g | 0.03 | 0.06 | 0.04 RRT0.51 | 0.06 | 0.04 RRT0.51 | 0.09 | 0.71 RRT0.51 | 0.87 | 0.13 RRT0.94 | 0.32 |

Table 1 shows the results of the impurity content changes in the mixed powder of the active ingredient and the excipients after 10 days of stress testing, and the corresponding risk levels are classified according to the following criteria:

Level 1 (low risk): maximum single impurity is less than 0.1% and total impurity is less than 0.2%;

Level 2 (medium risk): maximum single impurity is 0.1-0.2% or total impurity is 0.2%-0.4%;

Level 3 (high risk): maximum single impurity is more than 0.2% or total impurity is more than 0.4%.

TABLE 2

Risk assessment of the API and excipients compatibility

| Excipient Type | Excipient Name | API/excipient ratio | RH75% | RH92.5% | 60° C. | Illumination | Total |
|---|---|---|---|---|---|---|---|
| Filler | Lactose | 1:10 | 1 | 1 | 1 | 2 | 5 |
| | Microcrystalline cellulose | 1:10 | 1 | 1 | 3 | 2 | 7 |
| | Microcrystalline cellulose-lactose compound | 1:10 | 1 | 1 | 2 | 2 | 6 |
| | Mannitol | 1:10 | 1 | 1 | 1 | 2 | 5 |
| | Pregelatinized starch | 1:10 | 2 | 2 | 3 | 2 | 9 |
| | Starch | 1:10 | 2 | 2 | 3 | 2 | 9 |
| | Starch-lactose compound | 1:10 | 1 | 1 | 1 | 2 | 5 |
| Stabilizer | Tartaric acid | 1:10 | 1 | 1 | 1 | 2 | 5 |
| | Citric acid | 1:10 | 1 | 1 | 1 | 2 | 5 |
| | Malic acid | 1:10 | 1 | 1 | 2 | 2 | 6 |
| Disintegrant | Crospovidone | 1:10 | 1 | 1 | 2 | 2 | 6 |
| | Sodium carboxymethyl starch | 1:10 | 3 | 3 | 3 | 2 | 11 |
| | Cross-linked sodium carboxymethyl cellulose | 1:10 | 2 | 1 | 2 | 2 | 7 |
| | L-HPC | 1:10 | 2 | 2 | 3 | 2 | 9 |
| Lubricant | Magnesium stearate | 1:10 | 1 | 2 | 3 | 2 | 8 |
| | Sodium stearyl fumarate | 1:10 | 1 | 3 | 3 | 2 | 9 |
| | Glyceryl behenate | 1:10 | 1 | 1 | 1 | 3 | 6 |
| Adhesive | Povidone K29/32 | 1:10 | 1 | 1 | 3 | 2 | 7 |
| Glidant | Colloidal silica | 1:5 | 1 | 1 | 1 | 2 | 5 |
| Empty capsule | Empty gelatin capsule | Packing | 1 | 1 | 3 | 1 | 6 |
| | Empty HPMC capsule | Packing | 1 | 1 | 1 | 1 | 4 |
| Coating powder ingredient | PVA | 1:10 | 3 | 3 | 3 | 2 | 11 |
| | HPMC | 1:10 | 1 | 1 | 3 | 2 | 7 |
| | Triacetin | 1:10 | 2 | 2 | 2 | 2 | 8 |
| | TiO$_2$ | 1:10 | 1 | 1 | 3 | 3 | 8 |
| API | Neptinib xylenesulfonate | | 1 | 1 | 1 | 2 | 5 |

From the risk assessment results in Table 2 it is clear that the compositions comprising one or more ingredients of starch, pregelatinized starch, microcrystalline cellulose, sodium carboxymethyl starch, L-HPC, magnesium stearate, sodium stearyl fumarate and PVA present a higher risk. While the compositions with one or several ingredients selected from lactose, mannitol, microcrystalline cellulose-lactose compound, starch-lactose compound, tartaric acid, citric acid, crospovidone, colloidal silica, and glyceryl behenate were identified low risks of compatibility.

Example 2: Preparation of Dosage Forms

The following examples show a method of preparing the dosage forms comprising neptinib xylenesulfonate as the active ingredient.

2.1 Preparation of Capsules and Powder Dosage Form of Neptinib Xylenesulfonate

TABLE 3

The contents and compositions for preparation of capsules and powder dosage form of neptinib xylenesulfonate

| Component | Specification 1 | Specification 2 | Specification 3 | Specification 4 |
|---|---|---|---|---|
| Neptinib xylenesulfonate | 1.78 mg (1 mg neptinib) | 5.33 mg (3 mg neptinib) | 8.88 mg (5 mg neptinib) | 17.76 mg (10 mg neptinib) |

TABLE 3-continued

The contents and compositions for preparation of capsules and powder dosage form of neptinib xylenesulfonate

| Component | Specification 1 | Specification 2 | Specification 3 | Specification 4 |
|---|---|---|---|---|
| (calculated on the anhydrous basis) | | | | |
| Mannitol | 120.78 mg | 138.12 mg | 236.12 mg | 276.24 mg |

TABLE 3-continued

The contents and compositions for preparation of capsules and powder dosage form of neptinib xylenesulfonate

| Component | Specification 1 | Specification 2 | Specification 3 | Specification 4 |
|---|---|---|---|---|
| Colloidal silica | 1.25 mg | 1.5 mg | 2.5 mg | 3.0 |
| Glyceryl behenate | 1.25 mg | 1.5 mg | 2.5 mg | 3.0 mg |
| Total weight | 125 mg | 150 mg | 250 mg | 300 mg |

Preparation method: according to the contents and compositions shown in Table 3, the active ingredient neptinib xylenesulfonate was first passed through a 60-100 mesh sieve, and then mixed with mannitol, colloidal silica, glyceryl behenate and passed through a 40-60 mesh sieve together, yielding the final blending material. The finial blending material was directly placed in an automatic capsule filling machine, and filled to empty gelatin capsules of sizes 4#, 3# or 2# based on the weight of the contents.

2.2 Preparation of Granule Dosage Form of Neptinib Xylenesulfonate

TABLE 4

The contents and compositions for preparation of granule dosage form of neptinib xylenesulfonate

| Component | Specification 1 | Specification 2 | Specification 3 | Specification 4 |
|---|---|---|---|---|
| Neptinib xylenesulfonate (calculated on the anhydrous basis) | 1.78 mg (1 mg neptinib) | 5.33 mg (3 mg neptinib) | 8 88 mg (5 mg neptinib) | 17.76 mg (10 mg neptinib) |
| Lactose monohydrate | 120.78 mg | 138.12 mg | 236.12 mg | 276.24 mg |
| Colloidal silica | 1.25 mg | 1.5 mg | 2.5 mg | 3.0 |
| Glyceryl behenate | 1.25 mg | 1.5 mg | 2.5 mg | 3.0 mg |
| Total weight | 125 mg | 150 mg | 250 mg | 300 mg |

Preparation method: According to the contents and compositions shown in Table 4, the active ingredient neptinib xylenesulfonate was first passed through a 60-100 mesh sieve, and then was mixed with lactose monohydrate in a high-speed shear granulator. Purified water was added for granulation, and then was dried at 50-60° C. The dried granules were finally blended with colloidal silica and glyceryl behenate and filled into composite film bags.

2.3 Preparation of Tablets of Neptinib Xylenesulfonate
2.3.1

TABLE 5

The contents and compositions for preparation of tablets of neptinib xylenesulfonate

| Component | Specification 1 | Specification 2 | Specification 3 | Specification 4 |
|---|---|---|---|---|
| Neptinib xylenesulfonate (calculated on the anhydrous basis) | 1.78 mg (1 mg neptinib) | 5.33 mg (3 mg neptinib) | 8.88 mg (5 mg neptinib) | 17.76 mg (10 mg neptinib) |
| Lactose monohydrate | 31.1 mg | 37.8 mg | 44.5 mg | 89.0 mg |
| Mannitol | 62.12 mg | 75.62 mg | 89.12 mg | 178.24 mg |
| Crospovidone | 3.0 mg | 3.75 mg | 4.5 mg | 9 mg |
| Colloidal silica | 1.0 mg | 1.25 mg | 1.5 mg | 3 mg |
| Glyceryl behenate | 1.0 mg | 1.25 mg | 1.5 mg | 3 mg |
| Opadry coating powder | 4 mg | 5 mg | 6 mg | 12 mg |
| Total weight | 104 mg | 130 mg | 156.0 mg | 312.0 |

Preparation method: according to the contents and compositions shown in Table 5, the active ingredient neptinib xylenesulfonate was first passed through a 60-100 mesh sieve, the other excipients were passed through a 40-60 mesh sieve. Then they were subjected to final blending and compressing, and compressed into core tablets with diameter of 6 mm, 6 mm, 7 mm and 9 mm respectively, according to the specifications 1-4. The coating material (HPMC, triacetin or titanium dioxide) was sprayed on the core tablets. The surface temperature of the tablets was controlled in the range of 40-55° C. during film coating.

2.3.2

TABLE 6

The contents and compositions for preparation of tablets of neptinib xylenesulfonate

| Component | Specification 1 |
|---|---|
| Neptinib xylenesulfonate (calculated on the anhydrous basis) | 8.88 mg (5 mg neptinib) |
| Lactose monohydrate | 44.5 mg |
| Microcrystalline cellulose | 89.12 mg |
| Crospovidone | 4.5 mg |
| Colloidal silica | 1.5 mg |

TABLE 6-continued

The contents and compositions for preparation of tablets of neptinib xylenesulfonate

| Component | Specification 1 |
|---|---|
| Magnesium stearate | 1.5 mg |
| Opadry coating powder | 6 mg |
| Total weight | 156.0 mg |

Preparation method: same as in Example 2.3.1.

2.3.3

TABLE 7

The contents and compositions for preparation of tablets of neptinib xylenesulfonate

| Component | Specification 1 |
|---|---|
| Neptinib xylertesulfonate (calculated on the anhydrous basis) | 8.88 mg (5 mg Neptinib) |
| Lactose monohydrate | 44.5 mg |
| Pregelatinized starch | 89.12 mg |
| Crospovidone | 4.5 mg |
| Colloidal silica | 1.5 mg |
| Magnesium stearate | 1.5 mg |
| Opadry coating powder | 6 mg |
| Total weight | 156.0 mg |

Preparation method: same as in Example 2.3.1.

2.3.4

TABLE 8

The contents and compositions for preparation of tablets of neptinib xylenesulfonate

| Component | Specification 1 |
|---|---|
| Neptinib xylenesulfonate (calculated on the anhydrous basis) | 8.88 mg (5 mg Neptinib) |
| Lactose monohydrate | 44.5 mg |
| Microcrystalline cellulose | 89.12 mg |
| Sodium carboxymethyl cellulose | 4.5 mg |
| Colloidal silica | 1.5 mg |
| Magnesium stearate | 1.5 mg |
| Opadry coating powder | 6 mg |
| Total weight | 156.0 mg |

Preparation method: same as in Example 2.3.1.

2.3.5 Preparation of Neptinib Xylenesulfonate Tablets Containing a Stabilizer

TABLE 9

The contents and compositions for preparation of tablets of neptinib xylenesulfonate

| Component | Specification 1 | Specification 2 | Specification 3 | Specification 4 |
|---|---|---|---|---|
| Neptinib xylenesulfonate (calculated on the anhydrous basis) | 1.78 mg (1 mg Neptinib) | 5.33 mg (3 mg Neptinib) | 8.88 mg (5 mg Neptinib) | 17.76 mg (10 mg Neptinib) |
| Lactose monohydrate | 22.1 mg | 26.6 mg | 39.5 mg | 79.1 mg |
| Mannitol | 44.12 mg | 53.07 mg | 79.12 mg | 158.14 mg |
| Crospovidone | 2.4 mg | 3.0 mg | 4.5 mg | 9 mg |
| Colloidal silica | 0.8 mg | 1.0 mg | 1.5 mg | 3 mg |
| Glyceryl behenate | 0.8 mg | 1.0 mg | 1.5 mg | 3 mg |
| Tartaric acid | 8 | 10 | 15 | 30 |
| Opadry coating powder | 3.2 mg | 4 mg | 6 mg | 12 mg |
| Total weight | 83.2 mg | 104 mg | 156.0 mg | 312.0 |

Preparation method: The active ingredient neptinib xylenesulfonate was first passed through a 60-100 mesh sieve. Tartaric acid was crushed and then passed through an 80-120 mesh sieve. The sieved neptinib, tartaric acid and colloidal dioxide were pre-mixed, then subjected to final blending together with other excipients and compressing. The blending material was compressed into core tablets with diameter of 6 mm, 6 mm, 7 mm and 9 mm respectively, according to the specifications 1-4. The coating material (HPMC, triacetin or titanium dioxide) was sprayed on the core tablets. The surface temperature of the tablets was controlled in the range of 40-55° C. during film coating.

2.3.6 Preparation of Neptinib Xylenesulfonate Tablets Containing a Stabilizer

TABLE 10

The contents and compositions for preparation of tablets of neptinib xylenesulfonate

| Component | Specification 1 | Specification 2 | Specification 3 | Specification 4 |
|---|---|---|---|---|
| Neptinib xylenesulfonate (calculated on the anhydrous basis) | 1.78 mg (1 mg Neptinib) | 5.33 mg (3 mg Neptinib) | 8.88 mg (5 mg Neptinib) | 17.76 mg (10 mg Neptinib) |
| Lactose monohydrate | 22.1 mg | 26.6 mg | 39.5 mg | 79.1 mg |
| Mannitol | 44.12 mg | 53.07 mg | 79.12 mg | 158.14 mg |
| Crospovidone | 2.4 mg | 3.0 ma | 4.5 mg | 9 mg |
| Colloidal silica | 0.8 mg | 1.0 mg | 1.5 mg | 3 mg |
| Glyceryl behenate | 0.8 mg | 1.0 mg | 1.5 mg | 3 mg |
| Malic acid | 8 | 10 | 15 | 30 |
| Opadry coating powder | 3.2 mg | 4 mg | 6 mg | 12 mg |
| Total weight | 83.2 mg | 104 mg | 156.0 mg | 312.0 |

Preparation method: same as in Example 2.3.5.

Example 3: Detection of the Content of Impurity A

Accelerated stability test was carried out on the 5 mg coated tablets prepared in Example 2.2 and Example 2.3. The method for detecting impurity A and total impurity was shown as follows:

Equipment: Agilent 1260 series;
Column: XBridge Shield RP18 column (100×4.6 mm, 3.5 μm);
Mobile phase A: 0.05 mol/L potassium dihydrogen phosphate solution (adjusted to pH 7.2 with sodium hydroxide solution)-acetonitrile (20:80);
Mobile phase B: 0.05 mol/L potassium dihydrogen phosphate solution (adjusted to pH 7.2 with sodium hydroxide solution)-acetonitrile (40:60);

Linear gradient:

| Time (mm) | Mobile phase A | Mobile phase B |
|---|---|---|
| 0 | 74 | 26 |
| 8 | 54 | 46 |
| 20 | 54 | 46 |
| 30 | 0 | 100 |
| 40 | 0 | 100 |
| 40.1 | 26 | 74 |
| 45 | 26 | 74 |

Detection wavelength: 247 nm;
Flow rate: 1.0 ml/min;
Column temperature: 30° C.;
Injection volume: 10 μl;
Solvent: acetonitrile-water (50:50).

TABLE 11

Accelerated stability test results of Examples 2.3.1-2.3.4

| | Test time | | | | | |
|---|---|---|---|---|---|---|
| | 0 month | | 1 month | | 1.5 months | |
| Test condition | Impurity A % | Total impurity % | Impurity A % | Total impurity % | Impurity A % | Total impurity % |
| Example 2.3.1 (specification 5 mg) 40 ± 2° C., RH75 ± 5% | ND | 0.06 | 0.13 | 0.20 | 0.23 | 0.32 |
| Example 2.3.2 40 ± 2° C., RH75 ± 5% | ND | 0.06 | 0.35 | 0.86 | 0.54 | 1.41 |
| Example 2.3.3 40 ± 2° C., RH75 ± 5% | ND | 0.07 | 0.42 | 1.07 | 0.66 | 1.84 |
| Example 2.3.4 40 ± 2° C., RH75 ± 5% | ND | 0.06 | 0.81 | 1.76 | 1.33 | 2.12 |

From the above accelerated stability test results, it was found that within 0-1.5 months, the contents of impurity A and total impurity in the drug product of Examples 2.3.2, 2.3.3 and 2.3.4 was much higher than that of Example 2.3.1, and the impurity growth was significant. Therefore, the low-risk composition presented in the invention can effectively reduce the generation rate of impurity A.

TABLE 12

Accelerated stability test results of Example 2.3.1, Example 2.3.5 and Example 2.3.6

| Test condition | Test time | | | | | | | | | |
|---|---|---|---|---|---|---|---|---|---|---|
| | 0 month | | 1 month | | 2 months | | 3 months | | 6 months | |
| | Impurity A % | Total impurity % | Impurity A % | Total impurity % | Impurity A % | Total impurity % | Impurity A % | Total impurity % | Impurity A % | Total impurity % |
| Example 2.3.1 (specification 5 mg) 30 ± 2° C., RH65 ± 5% | 0.03 | 0.07 | 0.13 | 0.21 | 0.22 | 0.32 | 0.33 | 0.43 | 0.40 | 0.49 |
| Example 2.3.1 (specification 5 mg) 40 ± 2° C., RH75 ± 5% | 0.03 | 0.07 | 0.16 | 0.23 | 0.34 | 0.43 | 0.49 | 0.58 | 0.94 | 1.08 |
| Example 2.3.5 (specification 5 mg) 30 ± 2° C., RH65 ± 5% | 0.02 | 0.07 | 0.02 | 0.06 | 0.02 | 0.07 | 0.03 | 0.08 | 0.04 | 0.12 |
| Example 2.3.5 (specification 5 mg) 40 ± 2° C., RH75 ± 5% | 0.02 | 0.07 | 0.03 | 0.11 | 0.03 | 0.1 | 0.04 | 0.15 | 0.05 | 0.17 |
| Example 2.3.6 (specification 5 mg) 30 ± 2° C., RH65 ± 5% | 0.02 | 0.03 | 0.04 | 0.07 | 0.06 | 0.09 | 0.09 | 0.14 | 0.16 | 0.20 |
| Example 2.3.6 (specification 5 mg) 40 ± 2° C., RH75 ± 5% | 0.02 | 0.03 | 0.05 | 0.08 | 0.07 | 0.12 | 0.10 | 0.14 | 0.17 | 0.22 |

As shown in the above accelerated test stability results, although the pharmaceutical excipients with relative low risks of compatibility was used in the drug product of Example 23.1, the content of the specific impurity A in the drug product still increased significantly when it was tested for six months under conditions of longer period of time and higher temperature of the accelerated tests. Based on the composition of Example 2.3.1, the acid according to the present invention was added to obtain the compositions of Examples 2.3.5 and 2.3.6. As demonstrated by the results of the accelerated tests in Example 2.3.5 and Example 2.3.6, these specific compositions presented in this invention can overcome the issue of the impurity A controlling, ensuring that the content of impurity A does not increase significantly.

What is claimed is:

1. A pharmaceutical composition comprising neptinib, comprising the following components by weight:
   Neptinib or a pharmaceutically acceptable salt thereof 0.1%-7%
   Lactose and mannitol combination 70-96%
   Crospovidone 1-10%
   Colloidal silica 0.5-3%
   Glyceryl behenate 0.5-3%
   Stabilizer 0.1-15%,
   wherein the stabilizer is selected from the group consisting of benzoic acid, citric acid, tartaric acid, malic acid, edetic acid, and lactic acid.

2. The pharmaceutical composition according to claim 1, wherein the pharmaceutically acceptable salt of neptinib comprises neptinib dihydrochloride, neptinib dimaleate or neptinib xylenesulfonate.

3. The pharmaceutical composition according to claim 2, wherein the neptinib xylenesulfonate is a hydrate of neptinib xylenesulfonate.

4. The pharmaceutical composition according to claim 3, wherein the hydrate of neptinib xylenesulfonate comprises 1.0-1.5% crystal water in the neptinib xylenesulfonate molecule.

5. The pharmaceutical composition according to claim 1, wherein the stabilizer is selected from the group consisting of citric acid, tartaric acid and malic acid.

6. A preparation comprising the pharmaceutical composition of claim 1, wherein its dosage form is selected from the group consisting of tablet, capsule, granule, and powder.

7. A preparation comprising the pharmaceutical composition of claim 1, wherein its dosage form is tablet coated with HPMC film.

* * * * *